United States Patent
Sakata

[11] Patent Number: 5,242,832
[45] Date of Patent: Sep. 7, 1993

[54] REAGENT FOR MEASUREMENT OF LEUKOCYTES AND HEMOGLOBIN IN BLOOD

[75] Inventor: Takashi Sakata, Hyogo, Japan
[73] Assignee: TOA Medical Electronics Co., Ltd., Japan
[21] Appl. No.: 596,205
[22] Filed: Oct. 10, 1990
[30] Foreign Application Priority Data Mar. 1, 1990 [JP] Japan .................................. 2-50813
May 2, 1990 [JP] Japan .................................. 2-116658

[51] Int. Cl.$^5$ ...................... G01N 33/48; G01N 33/72
[52] U.S. Cl. .......................................... 436/17; 436/8;
436/10; 436/18; 436/63; 436/66; 436/176
[58] Field of Search ................... 436/8, 10, 11, 12, 13,
436/14, 15, 16, 17, 18, 19, 66, 21, 176, 63

[56] References Cited

U.S. PATENT DOCUMENTS

| | | | |
|---|---|---|---|
| 2,660,009 | 1/1954 | Stayner | 436/18 X |
| 4,185,964 | 1/1980 | Lancaster | 23/230 B |
| 4,213,876 | 7/1980 | Crews et al. | 436/10 X |
| 4,244,837 | 1/1981 | Crews et al. | 436/18 |
| 4,286,963 | 9/1981 | Ledis et al. | 436/18 |
| 4,286,963 | 9/1981 | Ledis et al. | 436/63 |
| 4,289,649 | 9/1981 | Harders et al. | 436/13 |
| 4,290,772 | 9/1981 | Frey | 436/18 X |
| 4,528,274 | 7/1985 | Carter et al. | 436/17 |
| 4,617,275 | 10/1986 | Matsuda et al. | 436/10 |
| 4,637,986 | 1/1987 | Brown et al. | 436/10 |
| 4,745,071 | 5/1988 | Lapicola et al. | 436/17 |
| 4,822,872 | 4/1989 | Kameyama et al. | 530/383 |
| 4,853,338 | 8/1989 | Benezra et al. | |
| 4,871,677 | 10/1989 | Baugh et al. | 436/176 |
| 5,116,539 | 5/1992 | Hamaguchi et al. | 436/10 X |

FOREIGN PATENT DOCUMENTS 0177137  4/1986  European Pat. Off.
8402777  7/1984  PCT Int'l Appl.
8403771  9/1984  PCT Int'l Appl.

OTHER PUBLICATIONS

Clinical Biochemistry, vol. 15, No. 1, 1982, pp. 83-88; I. Oshiro et al.: "New Method for Hemoglobin Determination by Using Sodium Lauryl Sulfate (SLS) Abstract"; p. 83, Col. 2, lines 1-10.

Chemical Abstracts, vol. 102, No. 23, 10th Jun. 1985, p. 321, abstract No. 2000716z, Columbus, Ohio, U.S. & JP-A-60 35 270 (Wako Pure Chemical Industries, Ltd.) Feb. 23, 1985.

*Primary Examiner*—James C. Housel
*Assistant Examiner*—Arlen Soderquist
*Attorney, Agent, or Firm*—Pearne, Gordon, McCoy & Granger

[57] ABSTRACT

A reagent, satisfying the undermentioned conditions, is useful for counting the number of leukocytes and measuring the hemoglobin concentration in blood samples. The reagent is free of cyanides and it is able to maintain hemoglobin in a stable state for a prolonged time. The reagent contains at least one cationic surfactant selected from the group consisting of a quaternary ammonium salt of a concentration capable of hemolyzing erythrocytes in the blood and oxidizing hemoglobin and a composition of pyridinium salts; at least one cationic, nonionic or amphoteric surfactant; and at least one hemoglobin stabilizer.

6 Claims, 6 Drawing Sheets

REAGENT FOR MEASUREMENT OF LEUKOCYTES AND HEMOGLOBIN IN BLOOD

FIELD OF THE INVENTION-DESCRIPTION OF RELATED ART

This invention relates to a reagent for measuring leukocytes and hemoglobin in blood samples.

Measurement of hemoglobin concentration and the number of leukocytes in a blood sample is crucial for clinical diagnoses of leukemia, anemia and other hemotopathys.

The basic method used for measuring or counting the number of leukocytes is a visual counting method with the aid of a microscope. However, with the visual counting method, the erythrocytes are hemolyzed by, for example, a Türk solution, while the leukocytes are stained and the number of leukocytes is counted one by one on a counting plate, which involves a time consuming and labor-intensive operation.

Meanwhile, in counting the number of leukocytes in a blood sample, methods employing an automatic blood analyzer are frequently employed. In counting the number of leukocytes by means of an automatic blood analyzer, an erythrocytolytic agent including a surfactant is added to a blood sample for selective hemolyzation of erythrocytes in the blood sample to produce a sample for leukocyte measurement in which only leukocytes remain. This sample is passed through narrow paths or orifices provided in a detection section in an automatic blood analyzer, whereby electrical or optical signals are generated at the detection section, the number of these signals being a measure of the number of leukocytes.

Recently, there has also evolved an apparatus in which the deformation which leukocytes undergo is reduced to a minimum through the use of improved erthrocytolytic agents and in which, during counting of the number of leukocytes, the leukocytes are classified into granulocytes, monocytes, lymphocytes and so on depending upon the difference in their signal intensities. With the use of this automatic blood analyzer, the leukocytes can be classified and counted far more easily than with the visual counting method.

On the other hand, measurement of hemoglobin concentration is usually conducted by means of a cyanmethemoglobin method. With this method, an erythrocytolytic agent containing a nonionic surfactant or the like is added to the blood sample to elute hemoglobin contained in erythrocytes, the eluted hemoglobin is oxidised by the action of an oxidizing agent, such as potassium ferricyanate, to produce methemoglobin and ultimately the cyanide ions are added to methemoglobin for converting methemoglobin into cyanmethemoglobin (HiCN) to produce a stable hemoglobin measurement sample. The hemoglobin concentration of the produced sample is measured by measuring the absorbance at a predetermined wavelength of the sample. This method is accepted worldwide as the standard method. Although the sample prepared in this manner is an extremely stable substance, the hemoglobin is oxidized by using an oxidizing agent and it takes slightly longer than 10 minutes before oxidation is terminated. For this reason, with the automatic blood analyzer, the composition of the erythrocytolytic agent is improved to shorten the time necessary for oxidation, so that the reaction may be terminated in about 1 minute to enable hemoglobin measurement. In addition, it is possible to measure the number of leukocytes simultaneously. However, since toxic cyanides are used with the cyanmethemoglobin method reagent handling may endanger the operator. In addition, after measurement the waste liquor must be disposed of after cyanide decomposition with the use of, for example, sodium hypochlorite, entailing an extremely laborious operation.

For this reason, there is also employed a method, known as an oxyhemoglobin method, whereby erythrocytes are hemolyzed only with nonionic surfactants for converting hemoglobin into oxyhemoglobin ($HbO_2$), without oxidizing hemoglobin to methemoglobin, for measuring the absorbance at a predetermined wavelength. With the oxyhemoglobin method, since cyanides are not used, there is no risk in handling the reagents, while there is no necessity of performing a troublesome operation of disposing of the waste liquor.

However, with the oxyhemoglobin method, a problem is raised that a blood sample having a high methemoglobin content cannot be measured accurately, since methemoglobin then may not be converted to oxyhemoglobin. As an example, Table 1 shows comparison data of the measured results obtained with the Example 1 of the present invention and the oxyhemoglobin method for cases wherein the methemoglobin contents are changed with the use of control blood. The control blood, which is used as a substance for controlling the analytical accuracy of the automatic blood analyzer is usually stored in a cooled state, and may exhibit a stable hemoglobin concentration for a prolonged time. However, during storage at higher than ambient temperature, hemoglobin in the blood is gradually converted into methemoglobin. Therefore, when the control blood stored at 22° C. is measured by the oxyhemoglobin method, as shown in Table 1, that portion of hemoglobin which has been converted into methemoglobin is unable to be measured such that the measured value of hemoglobin becomes gradually lower than the initial value over several days.

As an example, Table 2 shows comparison data of measured results obtained with the Example 10 of the present invention and the oxyhemoglobin method for various values of the methemoglobin contents of the blood samples. With the oxyhemoglobin method, the hemoglobin concentration is lowered with an increase in the methemoglobin content.

As a solution to this problem, a reagent for hemoglobin measurement comprised of dodecyl sodium sulfate or equal amounts of lauryl sodium sulfate (SLS), an anionic surfactant, and Triton X-100, a nonionic surfactant, in a neutral buffer (pH, 7.2), is taught by Oshiro et al in Clinical Biochemistry, vol. 15, 83 (1982). With this method, erythrocytes are hemolyzed by the action of SLS and Triton X-100 and the eluted hemoglobin is converted into methemoglobin by the action of SLS at the same time that it is converted into SLS hemoglobin. With this method, the hemoglobin concentration in the blood may be measured without being affected by methemoglobin, while there is no necessity of disposing of the waste liquor because of the absence of cyanide contents. However, it is not possible with this method to measure leukocytes simultaneously with hemoglobin measurement. The Japanese Patent Public Disclosure (KOKAI) No. 61-148369 (1986) entitled "CYANIDE-FREE HEMOGLOBIN REAGENT" discloses a reagent for hemoglobin measurement with the aid of an ionic surfactant. However, it is similarly not possible with this reagent to measure the leukocytes simultaneously with the hemoglobin.

As discussed hereinabove, it is not possible with the prior-art technology to measure hemoglobin and leukocytes simultaneously by a cyanide-free reagent or to make a correct measurement of hemoglobin in a blood sample with a high methemoglobin content.

TABLE 1

| Results of Measurement of Control Blood (Oxyhemoglobin Method vs Example 1) | | |
|---|---|---|
| | Oxyhemoglobin Method | Example 1 |
| initial value | 16.0 g/l | 17.0 g/l |
| 22° C., stored for 3 days | 15.7 g/l | 17.0 g/l |
| 22° C., stored for 7 days | 15.5 g/l | 17.0 g/l |

TABLE 2

| Results of Measurement of Hemoglobin Concentration (Oxyhemoglobin Method vs Example 10) | | |
|---|---|---|
| Methemoglobin Contents | Oxyhemoglobin Method | Example 10 |
| 0% | 13.6 g/l | 13.6 g/l |
| 50% | 11.6 g/l | 13.6 g/l |
| 100% | 9.7 g/l | 13.6 g/l |

To solve the aforementioned problem, the present inventors have already proposed a reagent in Japanese Patent Public Disclosure (KOKAI) No. 1-275280 (1989).

With this reagent, the types and concentrations of the cationic, nonionic or amphoteric surfactants used as the erythrocytolytic agents or the oxidants are strictly defined to provide for substantially instantaneous elution of hemoglobin and conversion thereof into methemoglobin to enable measurement of leukocytes simultaneously with hemoglobin.

However, with this reagent, since it does not contain a methemoglobin stabilizing component, a problem arises in that the hemoglobin concentration changes slightly over a period of time after the preparation of the measurement samples, as shown in Comparative Example 4 of Table 3.

This, however, is not detrimental to the effect of the invention of the aforementioned Japanese Patent Public Disclosure because the time which elapses since the sample preparation until the time of measurement is short and strictly defined with the fully automated system of sample preparation and measurement.

There is also marketed a semi-automated system in which, for lowering the costs of the measurement system, sample preparation is made manually and only the measurement is performed by the system.

With the semi-automatic system, the time which elapses since sample preparation until the time of measurement fluctuates in the range of several to several tens of minutes.

For using the sample in the system, the hemoglobin concentration needs be stabilized at least for several tens of minutes after the time of sample preparation.

As discussed above, it is not possible with the prior-art technology to obtain a hemoglobin measurement sample which is cyanide-free and which will remain stable for a prolonged time and with which leukocytes may be measured simultaneously with hemoglobin and the hemoglobin contents in the blood sample with high methemoglobin contents may also be measured accurately.

SUMMARY OF THE INVENTION

As a result of lengthy research, however, the present inventors have arrived at the following reagent intended for the solution of the above-mentioned problems of the prior art.

In accordance with the present invention, there is provided a reagent, satisfying the undermentioned conditions, for counting the number of leukocytes and measuring the hemoglobin concentration in the blood, said reagent not containing cyanides and maintaining hemoglobin in a stable state for a prolonged time.

i) It contains at least one cationic surfactant of a concentration capable of hemolyzing erythrocytes in the blood and oxidizing hemoglobin selected from the group consisting of a quaternary ammonium salt (structure a) and a pyridinium salt (structure b):

structure a

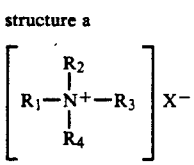

$R_1$: $C_8$ to $C_{20}$ alkyl, alkenyl or alkynyl group;
$R_2$ to $R_4$: $C_1$ to $C_8$ alkyl, alkynyl or alkinyl group;
$X^-$: anionic group;

structure b

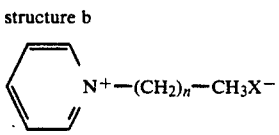

n: an integer of from 7 to 19;
$X^-$: an anionic group.

ii) It contains at least one selected from the group consisting of cationic, nonionic and amphoteric surfactants having the structures c to e:

structure c

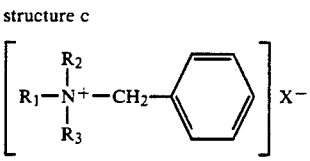

$R_1$: $C_8$ to $C_{20}$ alkyl, alkenyl or alkynyl group;
$R_2$ to $R_3$: $C_1$ to $C_8$ alkyl, alkenyl or alkynyl group;
$X^-$: anionic group;

structure d

$R_1$: $C_8$ to $C_{20}$ alkyl, alkenyl or alkynyl group;
$R_2$: O,

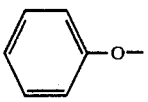

or COO;
n: an integer of from 10 to 50;

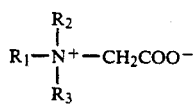    structure e $R_1$: $C_8$ to $C_{20}$ alkyl group;
$R_2$ to $R_3$: $C_1$ to $C_8$ alkyl, alkenyl or alkynyl group.

iii) It contains at least one of hemoglobin stabilizers f to o with the concentration as shown at f to o:

(f) Tiron with a concentration of 0.1 to 1000 mg/l:

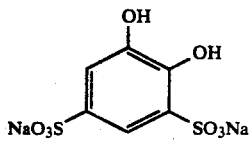

(g) 8-hydroxyquinoline with a concentration of 0.1 to 1000 mg/l:

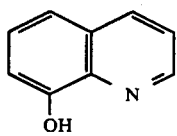

(h) bipyridine with a concentration of 10 to 10000 mg/l:

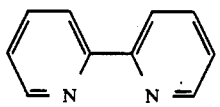

(i) 1,10-phenanthroline and its derivatives with a concentration of 10 to 3000 mg/l:

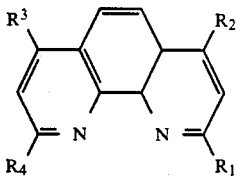

$R_1$, $R_4$: —H, —$CH_3$;
$R_2$, $R_3$: —H, phenyl group, —OH;

(j) phenolic compounds with a concentration of 0.1 to 1000 mg/l:

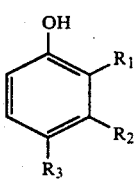

$R_1$: —H, $CH_2OH$, —CHO, —COOH or —OH;
$R_2$: —H, —COOH or —OH;
$R_3$: —H or —COOH;

(k) bisphenol A with a concentration of 0.1 to 1000 mg/l:

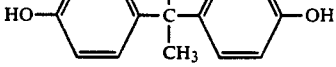

(l) pyrazole and its derivatives with a concentration of 0.1 to 10000 mg/l:

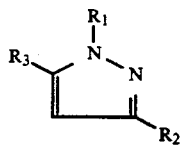

$R_1$, $R_2$, $R_3$: —H or $C_1$ to $C_4$ lower alkyl group;

(m) phenyl 5-pyrazolone and its derivative with a concentration of 0.1 to 10000 mg/l:

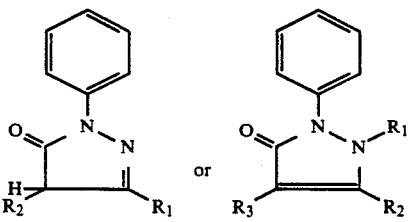

$R_1$, $R_2$, $R_3$: —H or $C_1$ to $C_4$ lower alkyl group;

(n) phenyl 3-pyrazolone with a concentration of 0.1 to 10000 mg/l:

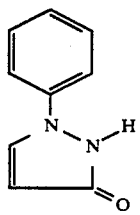

(o) imidazole and its derivatives with a concentration of 1 to 20000 mg/l:

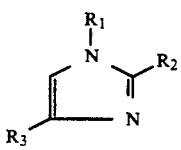

$R_1$, $R_2$: —H or $C_1$ to $C_4$ lower alkyl group;
$R_3$: —H or $C_1$ to $C_4$ lower alkyl group or phenyl group.

iv) It is a solution with a pH ranging between 3.0 and 9.0.

v) The total concentration of the quaternary ammonium salt is in the range of from 0.1 to 15.0 g/l.

vi) The total concentration of the pyridinium salt is in the range of from 0.1 to 15.0 g/l.

vii) The total concentration of the nonionic surfactant is in the range of from 0.1 to 15.0 g/l.

viii) The total concentration of the amphoteric surfactant is in the range of from 0.1 to 15.0 g/l.

ix) The total concentration of the cationic surfactant is in the range of from 0.1 to 15.0 g/l.

By suitably combining the components a to e in the reagent, leukocytes can be divided into two or three fractions, for example, into the fraction of lymphocytes, monocytes, eosinophilic leukocytes and basophilic leukocytes or neutrophilic leukocytes.

DETAILED DESCRIPTION OF THE DRAWINGS AND PREFERRED EMBODIMENTS

Figure 1:
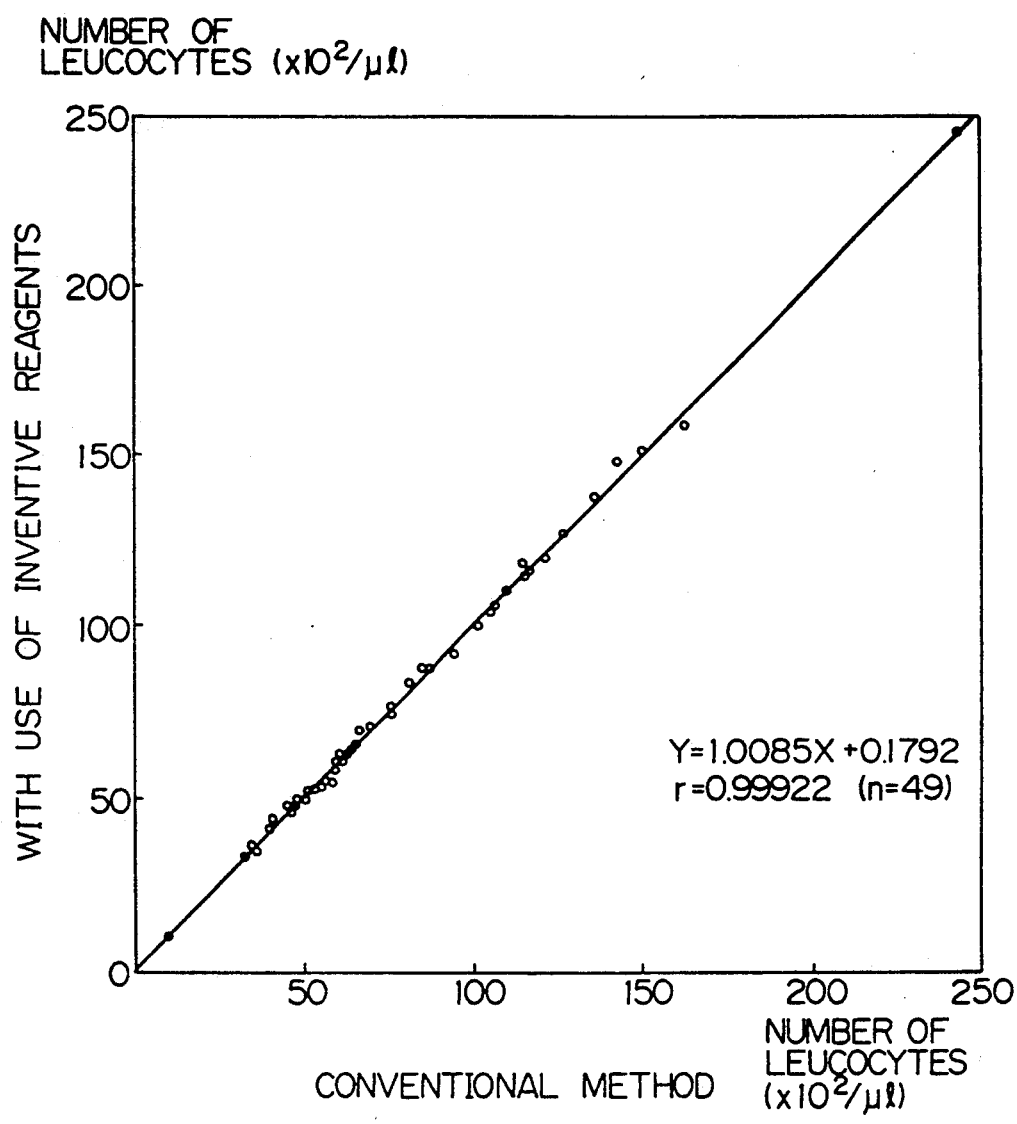
FIG. 1 shows a correlation between the results of measurement of the number of leukocytes by the conventional method using an F-800 apparatus manufactured by Toa Medical Electronics Co., Ltd. and the results of measurement of the number of leukocytes with the use of the reagent of the Example 1.

In general, for measuring the hemoglobin concentration, the hemoglobin in erythrocytes is eluted by the action of a suitable erythrocytolytic agent, the hemeferrum in the eluted hemoglobin is oxidized by the action of the erythrocytolytic agent and the oxygen in the solution or by the action of a suitable oxidizing agent, the yielded methemoglobin is stabilized by the action of conventional methemoglobin stabilizers, such as cyanide ions, and the absorbance of the stabilized hemoglobin sample is measured, as described previously. However, the use of the conventional methemoglobin stabilizer has been the cause of the aforementioned problem of disposal of resulting waste liquor. The methemoglobin free of methemoglobin stabilizer remains temporarily unstable as compared to the aforementioned cyanmethemoglobin or oxyhemoglobin, while its absorbance is changed with the pH value of the solution, so that it has not been used for hemoglobin measurement. The present inventors recently proposed in Japanese Patent Application No. 1-275280 (1989) a methemoglobin stabilizing reagent which is free from the abovementioned methemoglobin stabilizer. With this reagent, erythrocytes in the blood sample are selectively hemolyzed by the action mainly of quaternary ammonium salts or pyridinium salts for eluting hemoglobin in erythrocytes. The eluted hemoglobin is denatured, that is, modified in its steric structure, almost instantaneously, and hemeferrum in hemoglobin is oxidized by the oxygen dissolved in the reagent from the bivalent iron into trivalent iron to yield methemoglobin.

If only one kind of the cationic surfactant is used, a problem similar to that encountered with methemoglobin prepared without methemoglobin stabilizer is presented. However, with the reagent of Japanese Patent Application No. 1-275280 (1989), suitable amounts of cationic, nonionic and amphoteric surfactants are added thereto to adjust the degree of denaturation of hemoglobin to yield stable hemoglobin. The effects of the pH may be eliminated by addition of a buffer as will be explained subsequently. Although the methemoglobin stabilizing mechanism has not been clarified, it may be presumed that the action of plural surfactants with different molecular structures on hemoglobin possibly results in fixing the degree of denaturation or change in steric structure into methemoglobin at a predetermined level. With the reagent of Japanese Patent Application No. 1-275280 (1989), the number of leukocytes can be measured simultaneously since the leukocytes remain unchanged.

With the reagent of the present invention, the above-mentioned hemoglobin stabilizer is added to stabilize methemoglobin. The effect of the hemoglobin stabilizer is shown in Table 3.

Although the operating mechanism of the hemoglobin stabilizer of the present invention has not been clarified, it may be presumed that lone electron pairs of nitrogen atoms in the molecular structure of the hemoglobin stabilizer or oxygen atoms in the phenolic hydroxy groups may chelate with hemeferrum in methemoglobin resulting in stabilizing methemoglobin.

With the present reagent, the leukocytes may be divided into two or more fractions, subject to more strict limitations of surfactant concentrations.

The following are some of the compositional examples of the reagent according to the present invention.

| | Concentration Range |
|---|---|
| Compositional Example 1 | |
| lauryltrimethylammonium chloride (quaternary ammonium salt) | 0.1 to 15.0 g |
| lauryldimethylaminoacetic acid betaine (amphoteric surfactant) | 0.1 to 15.0 g |
| Tiron | 0.1 to 1000 mg |
| phosphate buffer | 1/15 to 1/60M |
| sodium chloride | 1.0 to 10.0 g |
| distilled water | 1 l |
| Compositional Example 2 | |
| myristyltrimethylammonium bromide (quaternary ammonium salt) | 0.1 to 12.0 g |
| polyoxyethylene nonylphenylether (nonionic surfactant) | 0.1 to 12.0 g |
| Tiron | 0.1 to 1000 mg |
| phosphate buffer | 1/15 to 1/60M |
| sodium chloride | 1.0 to 10.0 g |
| distilled water | 1 l |
| Compositional Example 3 | |
| lauryltrimethylammonium chloride (quaternary ammonium salt) | 0.3 to 10.0 g |
| cetyltrimethylammonium chloride (quaternary ammonium salt) | 0.01 to 2.0 g |
| Tiron | 0.1 to 1000 mg |
| phosphate buffer | 1/15 to 1/60M |
| sodium chloride | 1.0 to 10.0 g |
| distilled water | 1 l |

The reagents of the Compositional Examples 1 to 3 are prepared by hemolyzing and eluting erythrocytes by the action of surfactants such as quaternary ammonium salts or amphoteric surfactants to produce hemoglobin which is then converted into methemoglobin for stabilization and acted upon by Tiron for long term stabilization.

With the Compositional Example 1, the combination of quaternary ammonium salts and amphoteric surfactants is used to enable measurement of the leukocytes; with the Compositional Example 2, the combination of quaternary ammonium salts and nonionic surfactants is used to enable the leukocytes to be divided into at least two fractions; and with the Compositional Example 3, the combination of two different kinds of quaternary ammonium salts is used to enable the leukocytes to be divided into at least three fractions.

The term "total concentration of the quaternary ammonium salts" used in the claim means, in the case of Compositional Example 3, the concentration range of 0.31 to 12.0 g which is the sum of the concentration of lauryltrimethylammonium chloride and the concentration of cetyltrimethylammonium chloride.

|  | Concentration Range |
|---|---|
| Compositional Example 4 | |
| lauryltrimethylammonium chloride | 1.0 to 10.0 g |
| polyoxyethylene nonylphenylether | 1.0 to 10.0 g |
| 8-hydroxyquinoline | 0.1 to 1000 mg |
| phosphate buffer | 1/15 to 1/60M |
| sodium chloride | 1.0 to 10.0 g |
| distilled water | 1 l |
| Compositional Example 5 | |
| lauryltrimethylammonium chloride | 3.0 to 10.0 g |
| laurylbenzylammonium chloride (cationic surfactant) | 3.0 to 10.0 g |
| 1,10-phenanthroline | 10 to 3000 mg |
| phosphate buffer | 1/15 to 1/60M |
| sodium chloride | 1.0 to 10.0 g |
| distilled water | 1 l |
| Compositional Example 6 | |
| laurylpyridinium chloride (pyridinium salt) | 0.5 to 10.0 g |
| lauryldimethlaminoacetic acid betaine | 0.5 to 10.0 g |
| 1-phenyl-3-pyrazolone | 0.1 to 10000 mg |
| phosphate buffer | 1/15 to 1/20M |
| sodium chloride | 1.0 to 10.0 g |
| distilled water | 1 l |

With the Compositional Examples 4, 5 and 6, the combination of the quaternary ammonium salt, nonionic surfactant and 8-hydroxyquinoline, the combination of the quaternary ammonium salt, cationic surfactant and 1,10-phenanthroline and the combination of quaternary ammonium salt, pyridinium salt and 1-phenyl-3-pyrazolone, are used, respectively, for converting hemoglobin into methemoglobin for stabilization and the produced methemoglobin is then acted upon by a hemoglobin stabilizer or long-term stabilization.

With the present reagent, by controlling the surfactant concentration more rigorously, the leukocytes may be fractionated into two or three groups.

The following are further compositional examples of the reagent of the present invention.

|  | Concentration Range |
|---|---|
| Compositional Example 1 | |
| lauryltrimethylammonium chloride (quaternary ammonium salt) | 0.1 to 15.0 g |

|  | Concentration Range |
|---|---|
| lauryldimethylaminoacetic acid betaine (amphoteric surfactant) | 0.1 to 15.0 g |
| 4-phenylimidazole | 0.001 to 2.0 g |
| phosphate buffer | 1/15 to 1/60M |
| sodium chloride | 1.0 to 10.0 g |
| distilled water | 1 l |
| Compositional Example 8 | |
| myristyltrimethylammonium bromide (quaternary ammonium salt) | 0.1 to 12.0 g |
| polyoxyethylene nonylphenylether (nonionic surfactant) | 0.1 to 12.0 g |
| 4-phenylimidazole | 0.001 to 2.0 g |
| phosphate buffer | 1/15 to 1/60M |
| sodium chloride | 1.0 to 10.0 g |
| distilled water | 1 l |
| Compositional Example 9 | |
| lauryltrimethylammonium chloride (quaternary ammonium salt) | 0.3 to 10.0 g |
| cetyltrimethylammonium chloride (quaternary ammonium salt) | 0.01 to 2.0 g |
| 4-phenylimidazole | 0.001 to 2.0 g |
| phosphate buffer | 1/15 to 1/60M |
| sodium chloride | 1.0 to 10.0 g |
| distilled water | 1 l |

With the Compositional Examples 7 to 9, the erythrocytes are hemolyzed and eluted by the action of surfactants such as the quaternary ammonium salt or amphoteric surfactants to produce hemoglobin which is then converted into methemoglobin for stabilization and subsequently acted upon by 4-phenylimidazole to provide for long-term stabilization of hemoglobin.

With the Compositional Example 7, the combination of the quaternary ammonium salt and the amphoteric surfactant is used to enable measurement of the leukocytes; with the Compositional Example 8, the combination of the quaternary ammonium salt and the nonionic surfactant is used to enable the leukocytes to be divided into at least two fractions; and with the Compositional Example 9, the combination of two different types of the quaternary ammonium salts is used to enable the leukocytes to be divided into at least three fractions.

| Compositional Example 10 | Concentration Range |
|---|---|
| lauryltrimethylammonium chloride | 1.0 to 10.0 g |
| polyoxyethylene nonylphenylether | 1.0 to 10.0 g |
| imidazole | 0.3 to 20.0 mg |
| phosphate buffer | 1/15 to 1/60M |
| sodium chloride | 1.0 to 10.0 g |
| distilled water | 1 l |

Hemoglobin is stabilized by the action of the quaternary ammonium salt and the nonionic surfactant and the produced methemoglobin is further acted on by imidazole to effect long-term stabilization.

Meanwhile, it is possible, by adjusting the concentrations of the quaternary ammonium salt and the surfactants, to divide the leukocytes into two or more fractions. With the Compositional Example 1 to 10, the phosphate buffer is used to control the pH of the solution to be at an optional value within the range from 3.0 to 9.0. Thus, there is no limitation on the types of buffers, and any buffer other than a phosphate buffer, such as citrate, maleate or tris may be employed. The preferred pH range is from 5.0 to 8.0. If the pH value is 3.0 or less, damage to the leukocytes increases thus rendering measurement of the leukocytes difficult. If the pH value is 9.0 or more, the stability of hemoglobin deteriorates over time. Sodium chloride is used for adjusting electrical conductivity to a level able to be measured by an automatic blood analyzer and hence may be replaced by any inorganic or organic salts that may be dissociated into ions in an aqueous solution.

The concentrations of the various ingredients defined in the claim mean the concentrations under the state in which measurement may be made only by adding the blood to the reagent without the necessity of using other diluents. However, in the case of a conventional apparatus in which the diluent and the lysing reagents are mixed together at a predetermined ratio for measuring hemoglobin or leukocytes, it is possible to change the concentration of the ingredients of the various surfactants as a function of the mixing ratio of the apparatus, in which case the concentrations of the various ingredients defined in the claim means the concentrations in the liquid mixture consisting of the diluent and the lysing reagent.

In accordance with the present invention, i) hemoglobin concentration and leukocytes may be measured with a single reagent;

ii) even a blood sample having a high methemoglobin content may be measured;

iii) because cyanide is not contained, the troublesome operation of disposing of waste liquor may be eliminated; and iv) a reagent may be provided in which hemoglobin remains stable over a prolonged time.

With the use of the present reagent in an automatic blood analyzer, since there is no necessity of separately providing a hemoglobin measurement sample preparation section and a leukocyte measurement sample preparation section, the analyzer may be simplified in structure enabling a lowering in costs.

EXAMPLES

The reagents of the following compositions were prepared, and the effects derived from addition of the hemoglobin stabilizer shown in Table 3 are shown.

| | Concentration |
|---|---|
| lauryltrimethylammonium chloride | 1.25 g |
| lauryldimethylaminoacetic acid betaine | 1.00 g |
| maleate buffer | 1/60M (pH, 6.3) |
| sodium chloride | suitable amount (electrical conductivity is adjusted to about 13 ms/cm) |
| distilled water | 1 l |

TABLE 3

| | hemoglobin stabilizer | concentration mg/l | amount of change in hemoglobin concentration g/dl (rate of change: %) |
|---|---|---|---|
| Comp. Ex. 1 (international standard method) | — | — | 1.88 (−13.4) |
| Comp. Ex. 2 (automatic cyanmethemoglobin method) | — | — | −0.14 g (−1.0) |
| Comparative Example 3 | — | — | −0.60 (−4.3) |
| Comparative Example 4 | not added | — | −0.20 (−1.4) |
| Example 1 | Tiron | 300 | −0.06 (−0.4) |
| Example 2 | 8-hydroxyquinoline | 30 | −0.06 (−0.4) |
| Example 3 | bipyridine | 1000 | −0.10 (−0.7) |
| Example 4 | 1,10-phenanthroline | 100 | −0.14 (−1.0) |
| Example 5 | salicylic alcohol | 300 | −0.11 (−0.8) |
| Example 6 | bisphenol A | 30 | −0.10 (−0.7) |
| Example 7 | pyrazole | 1000 | −0.13 (−0.9) |
| Example 8 | 1-phenyl-3-pyrazolone | 1 | −0.08 (−0.6) |
| Example 9 | 3-methyl-1-phenyl 5-pyrazolone | 100 | −0.06 (−0.4) |
| Example 10 | imidazole | 1000 | −0.10 (−0.7) |
| Example 11 | 4-phenylimidazole | 100 | −0.08 (−0.6) |
| Example 12 | 2-ethylimidazole | 1000 | −0.10 (−0.7) |
| Example 13 | 1-methylimidazole | 1000 | −0.11 (−0.8) |

The changes in the hemoglobin concentration and the rates of change in Table 3 were computed by the following formulas:

Amount of change in hemoglobin concentration = (hemoglobin concentration measured in 30 minutes after sample preparation)-(hemoglobin concentration measured in 20 seconds after sample preparation)

Rate of change of hemoglobin = (amount of change of hemoglobin concentration)/hemoglobin concentration measured in 20 seconds after sample preparation) × 100 The F-800 measurement apparatus, produced by Toa Medical Electronics Co., Ltd., was used for all of the measurements.

With the Comparative Example 1 of Table 3, measurement was made using a cyanmethemoglobin method (international standard method) and, since it takes a long time to oxidize hemoglobin, the hemoglobin quantity is drastically changed since 20 seconds until 30 minutes after the sample preparation, as shown in Table 3. With Comparative Example 2, an automated cyanmethemoglobin method used in the automatic blood analyzer is used, in which the amount of change is substantially less.

With the Comparative Example 3, an example of hemoglobin measurement is shown, in which methemoglobin is produced using a sole surfactant (lauryltrimethylammonium chloride) excepting lauryldimethylaminoacetic acid betaine of the above composition. Since methemoglobin is not stabilized, the hemoglobin concentration is drastically changed since 20 seconds until 30 minutes after sample preparation.

In the Comparative Example 4 in which lauryldimethylaminoacetic acid betaine, an amphoteric surfactant, is added to the composition of Comparative Example 3, that is, a compositional example shown in Japanese Patent Application No. 1-275280 (1989), the rate of change is decreased as compared to that of Comparative Example 3.

With the compositions of the Examples 1 to 13 containing the hemoglobin stabilizer, the reagent of the present invention, the degree of change is further decreased as compared to the Comparative Example 4.

FIG. 1 shows the correlation between the results of measurement of the number of leukocytes by the conventional method employing F-800 apparatus produced by Toa Medical Electronics Co., Ltd. and the results of measurement of the number of leukocytes with the use of the reagent of Example 1.

The coefficient of correlation $r=0.999$ and the regression line $y=1.009x+0.179$, indicating an extremely high correlation.

Figure 2:
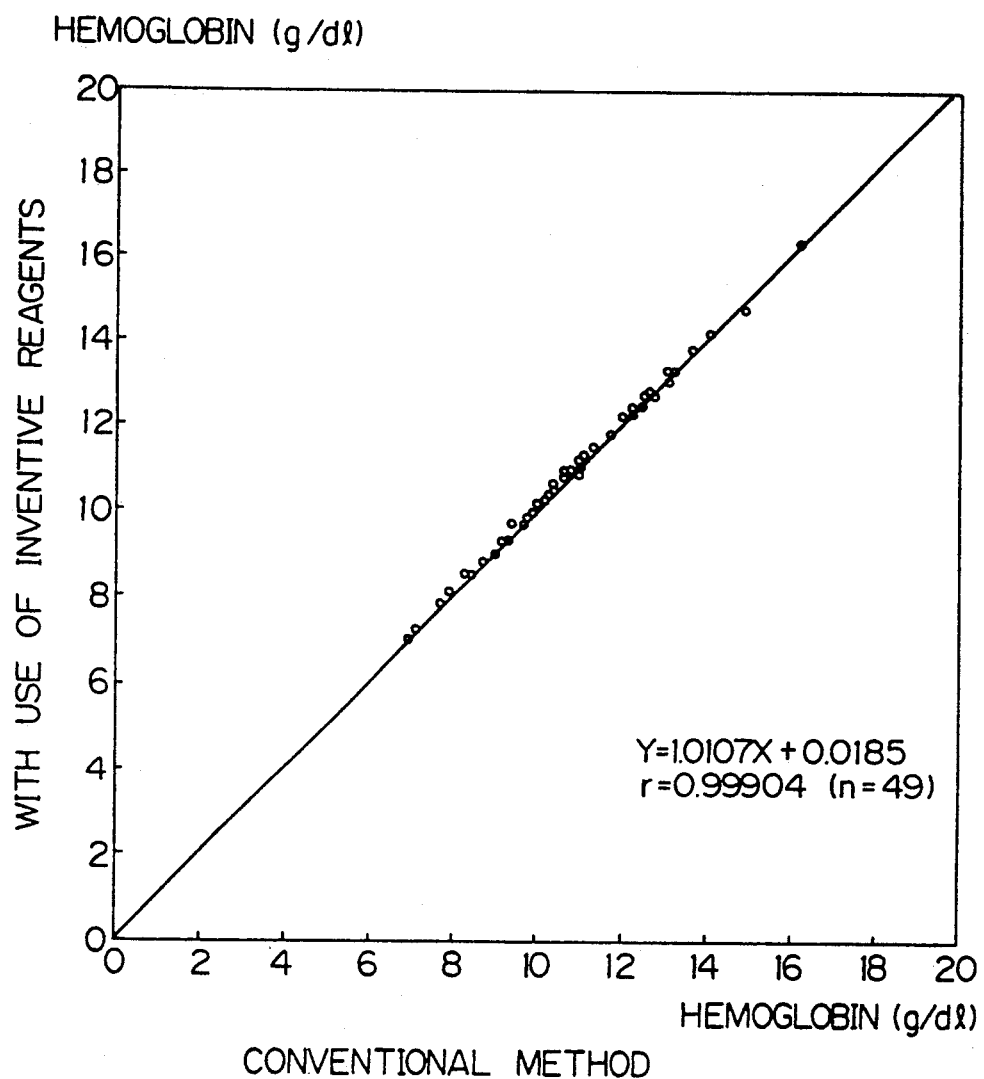
FIG. 2 shows a correlation between the results of measurement of the hemoglobin concentration by the conventional method, that is, the cyanmethemoglobin method, which is the international standard method, and the results of measurement of the hemoglobin concentration by the reagent of Example 1.

FIG. 2 shows the correlation between the results of measurement of hemoglobin concentration by the conventional method, that is the cyanmethemoglobin method (international standard method), and the results of measurement of the hemoglobin concentration with the use of the reagent of Example 1.

The coefficient of correlation $r=0.999$ and the regression line $y=1.011x+0.019$, indicating an extremely high correlation.

Figure 3:
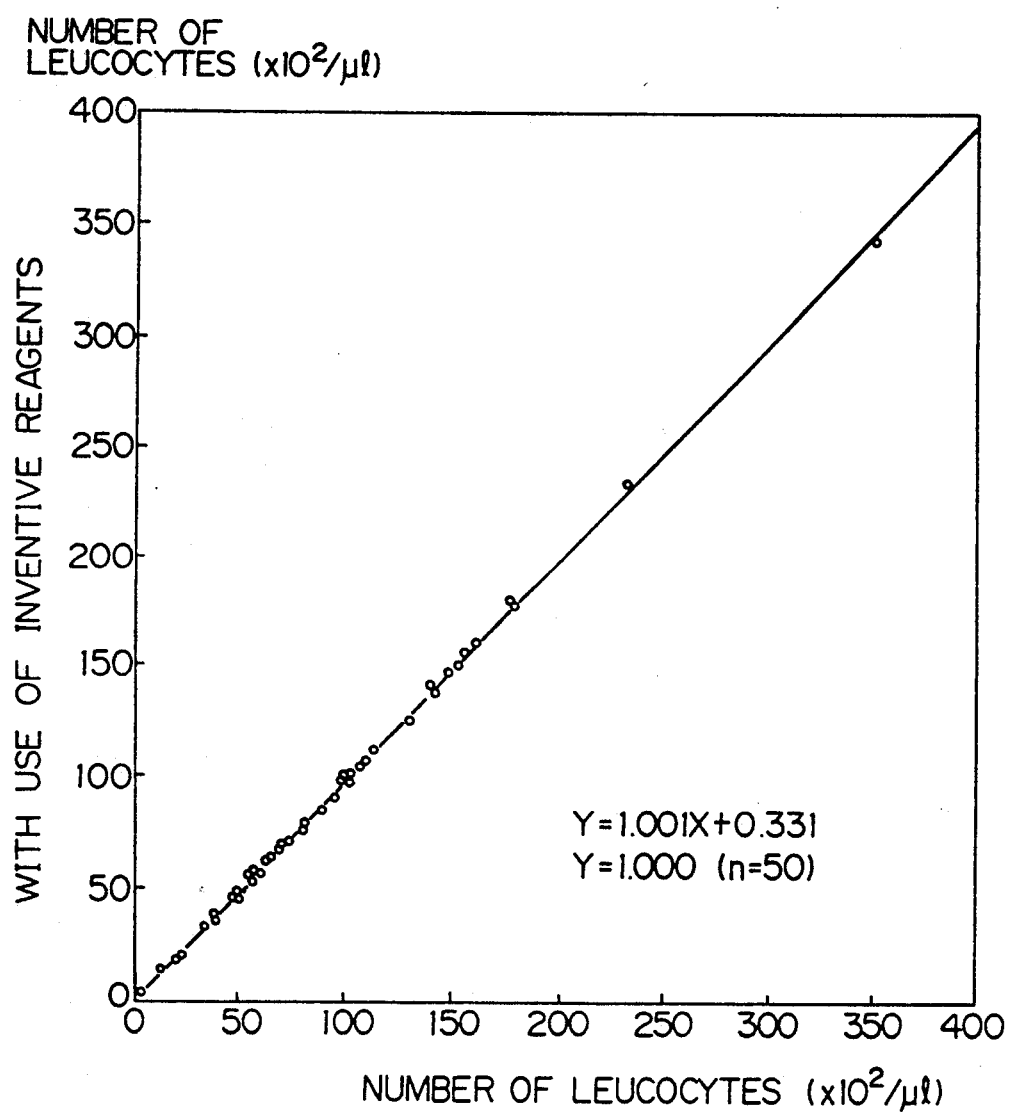
FIG. 3 shows a correlation between the results of measurement of the number of leukocytes by the conventional method using an F-800 apparatus produced by Toa Medical Electronics Co., Ltd. and the results of measurement of the number of leukocytes with the reagent of Example 10.

FIG. 3 shows the correlation between the results of measurement of leukocytes by the conventional method employing F-800 apparatus produced by Toa Medical Electronics Co., Ltd. and the results of measurement of the leukocytes with the use of the reagent of Example 10.

The coefficient of correlation $r=1.000$ and the regression line $y=1.001x+0.331$, indicating an extremely high correlation.

Figure 4:
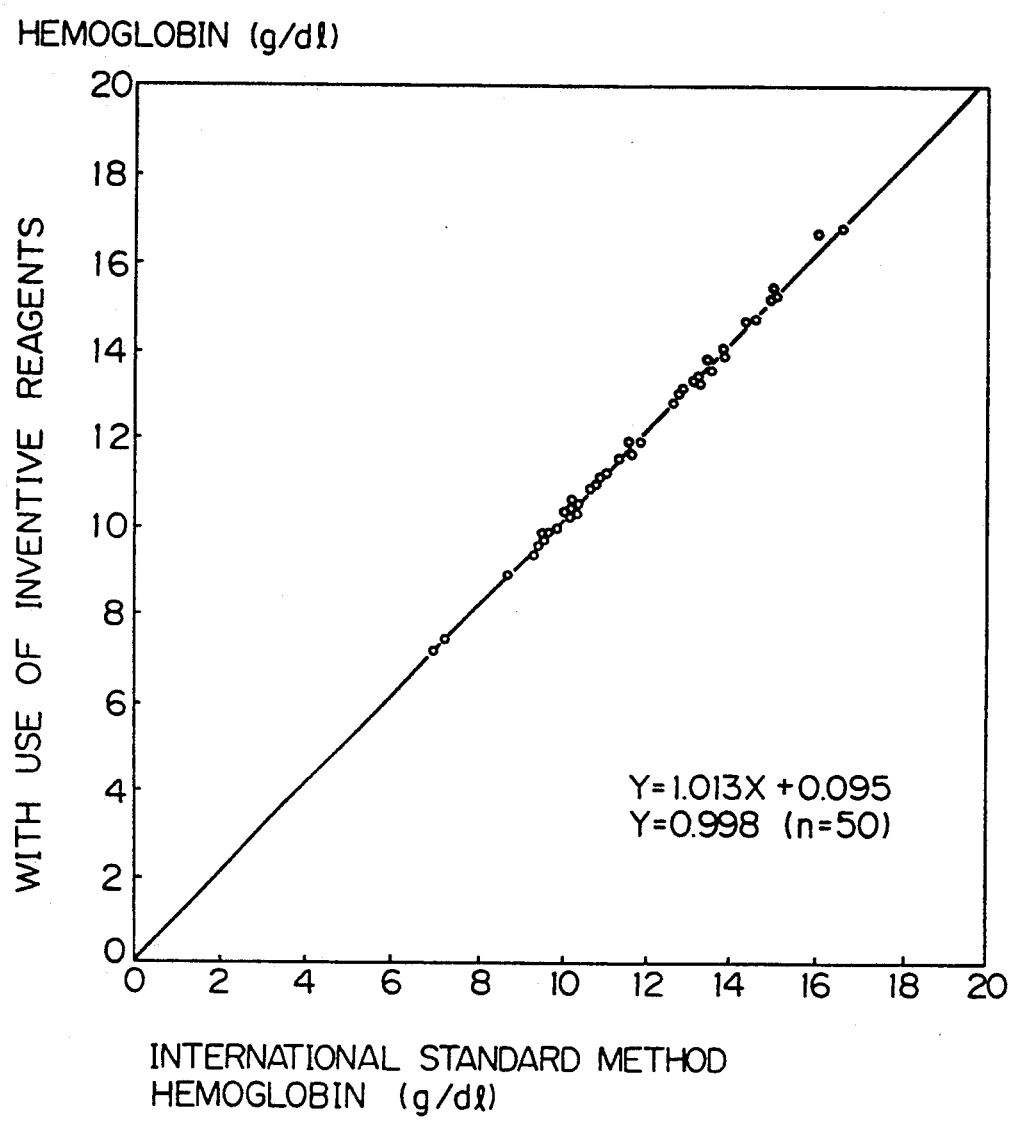
FIG. 4 shows a correlation showing the results of measurement of the hemoglobin concentration by the conventional method, that is, the cyanmethemoglobin method, which is the international standard method, and the results of measurement of the hemoglobin concentration with the reagent of Example 10.

FIG. 4 shows the correlation between the results of measurement of the hemoglobin concentration by the measurement of the hemoglobin concentration by the conventional cyanmethemoglobin method (international standard method) and the results of measurement of the hemoglobin concentration with the use of the reagent of Example 10.

The coefficient of correlation $r=0.998$ and the regression line $y=1.013x+0.095$, indicating an extremely high correlation.

As shown in Table 1, even when the hemoglobin concentration as measured by the oxyhemoglobin method is lowered as a result of an increase in the quantity of methemoglobin, the measurement value of hemoglobin concentration as measured with the reagent of Example 1 is not changed but remains constant.

Meanwhile, the difference between the initial value as obtained with the oxyhemoglobin method shown in Table 1 and the initial value as obtained with the reagent of the Example 1 is ascribable to the use of a control blood in which a predetermined quantity of hemoglobin in the blood has from the outset been converted into methemoglobin.

EXAMPLE 14

The reagent of the following composition was prepared.

| | Concentration |
| --- | --- |
| lauryltrimethylammonium chloride | 1.50 g |
| cetyltrimethylammonium chloride | 0.40 g |
| phosphate buffer | 1/25M (pH, 6.0) |
| sodium chloride | suitable amount (electrical conductivity is adjusted to about 13 ms/cm) |
| Tiron | 300 mg |
| distilled water | 1 l |

EXAMPLE 15

The reagent of the following composition was prepared.

| | Concentration |
| --- | --- |
| lauryltrimethylammonium chloride | 3.20 g |
| cetyltrimethylammonium chloride | 0.20 g |
| phosphate buffer | 1/25M (pH, 6.0) |
| sodium chloride | suitable amount (electrical conductivity is adjusted to about 13 ms/cm) |
| Tiron | 300 mg |
| distilled water | 1 l |

Figure 5:
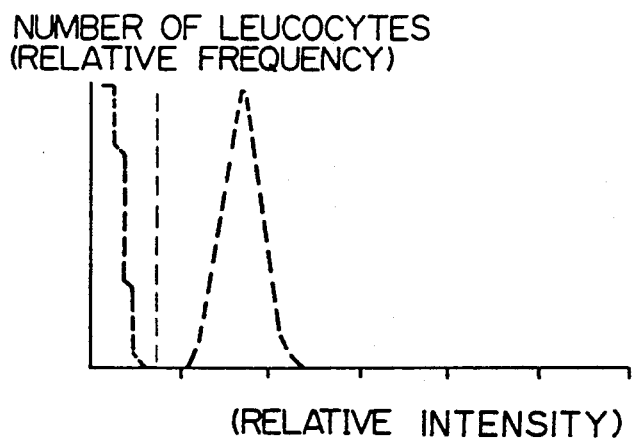
FIGS. 5 to 7 are charts showing the leukocyte size distribution with the use of the reagents of the Examples 1, 14 and 15, respectively.
Figure 6:
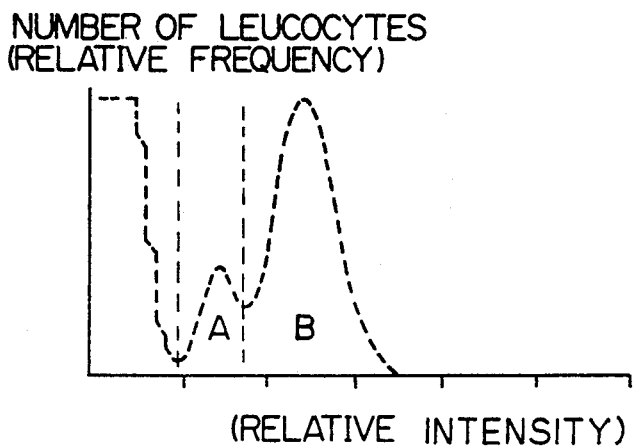
Figure 7:
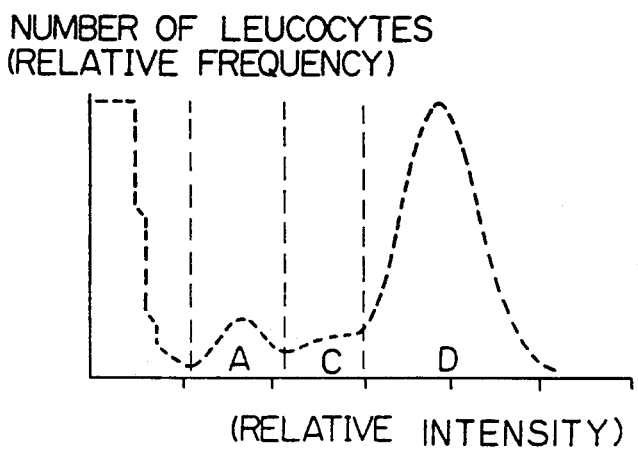

FIGS. 5 to 7 show the particle size distribution of the leukocytes with the use of the reagents of the Examples 1, 14 and 15, respectively. In these figures, the ordinate denotes the relative frequency of the blood cells, and the abscissa denotes the relative intensity of the blood cell signals, that is the size of the blood cells, obtained on measurement of the blood cells with the aid of the automatic blood analyzer. With the use of the reagent of Example 1, the leukocytes show a single-peak particle size distribution, as shown in FIG. 5. With the use of the reagent of the Example 14, the leukocytes show a particle size distribution composed of two regions A and B, as shown in FIG. 6. The region A stands for an aggregate of lymphocytes and the region B an aggregate of leukocytes other than the lymphocytes. With the use of the reagents of Example 15, the leukocytes show a particle size distribution composed of regions A, C and D, as shown in FIG. 7. The region A stands for an aggregate of lymphocytes, the region C an aggregate of monocytes, eosinophilic leukocytes and basophilic leukocytes and the region D stands for an aggregate of neutrophilic leukocytes.

As shown in Table 2, even when the hemoglobin concentration as measured by the oxyhemoglobin method is lowered due to an increased methemoglobin contents, the hemoglobin concentration as measured by the reagent of Example 10 is not changed but remains constant.

EXAMPLE 16

The reagent of the following composition was prepared.

| | Concentration |
| --- | --- |
| lauryltrimethylammonium chloride | 1.50 g |
| cetyltrimethylammonium chloride | 0.40 g |
| phosphate buffer | 1/25M (pH, 6.0) |
| sodium chloride | suitable amount (electrical conductivity is adjusted to about 13 ms/cm) |
| 4-phenylimidazole | 100 mg |
| distilled water | 1 l |

EXAMPLE 17

The reagent of the following composition was prepared.

|  | Concentration |
|---|---|
| lauryltrimethylammonium chloride | 3.20 g |
| cetyltrimethylammonium chloride | 0.20 g |
| phosphate buffer | 1/25M (pH, 6.0) |
| sodium chloride | suitable amount (electrical conductivity is adjusted to about 13 ms/cm) |
| 4-phenylimidazole | 100 mg |
| distilled water | 1 l |

Figure 8:
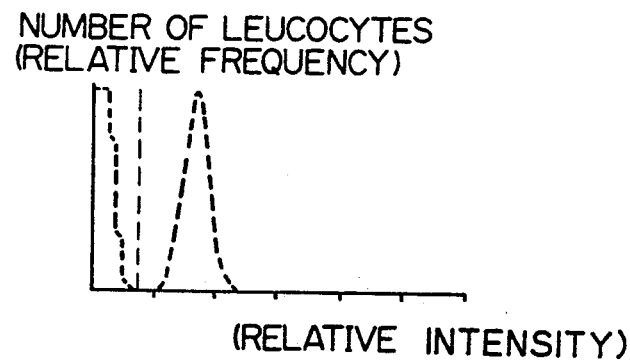
FIGS. 8 to 10 are charts showing the leukocyte size distributions with the use of the reagents of the Examples 10, 16 and 17, respectively.
Figure 9:
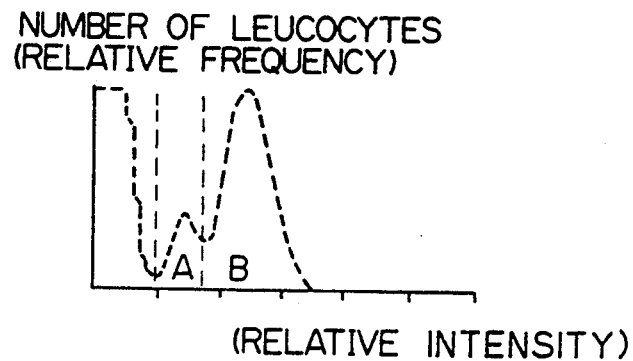
Figure 10:
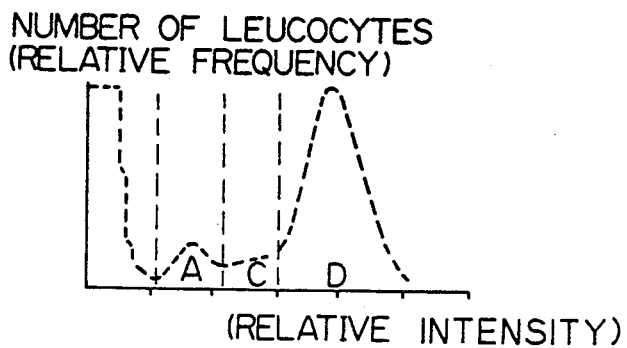

FIGS. 8 to 10 show the particle size distribution of the leukocytes with the use of the reagents of the Examples 10, 16 and 17, respectively. In these figures, the ordinate denotes the relative frequency of the blood cells, and the abscissa denotes the relative intensity of the blood cell signals, that is the size of the blood cells, obtained upon measurement of the blood cells with the aid of an automatic blood analyzer. With the use of the reagent of Example 10, the leukocytes indicate a single-peak particle size distribution, as shown in FIG. 8. With the use of the reagent of Example 16, the leukocytes indicate a particle size distribution composed of two regions A and B, as shown in FIG. 9. The region A stands for an aggregate of lymphocytes and the region B an aggregate of leukocytes other than the lymphocytes. With the use of the reagents of Example 17, the leukocytes indicate a particle size distribution composed of regions A, C and D, as shown in FIG. 10. The region A stands for an aggregate of lymphocytes, the region C an aggregate of monocytes, eosinophilic leukocytes and basophilic leukocytes and the region D stands for an aggregate of neutrophilic leukocytes.

From the foregoing, it is seen that, with the reagent of the present invention, not only the measured values which are the same as those of the prior art may be obtained, but i) the hemoglobin and leukocytes may be measured by one and the same sample, while the leukocytes may be fractionated;

ii) correct measurement may be achieved even with blood samples with high methemoglobin contents;

iii) since toxic substances, such as cyanides, are not used, it becomes unnecessary to dispose of waste liquor; and iv) the reagent may be supplied in which hemoglobin remains stable for an extended period of time.

What is claimed is:

1. A reagent for use in counting the number of leukocytes and measuring the hemoglobin concentration in a blood sample, said reagent not containing cyanides and being able to maintain hemoglobin in a substantially stable state for a prolonged time comprising:
a solution with a pH ranging from 3.0 to 9.0 containing:
i) at least one first surfactant, said at least one first surfactant being cationic and of a concentration capable of hemolyzing erythrocytes in the blood sample being quaternary ammonium salts of the formula:

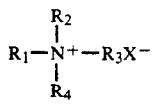

(a)

where
$R_1$ is a $C_8$ to $C_{20}$ alkyl, alkenyl or alkynyl group,
$R_2$ and $R_4$ is a $C_1$ to $C_8$ alkyl, alkenyl or alkynyl group,
$R_3$ is a $C_1$ to $C_8$ alkyl, alkenyl, alkynyl or benzyl group, and
$X^-$ is an anionic group;
said quaternary ammonium salts having a total concentration in the range of 0.1 to 15.0 g/l; and ii) at least one second surfactant selected from the group consisting of pyridinium salts and amphoteric surfactants, said pyridinium salts having the formula:

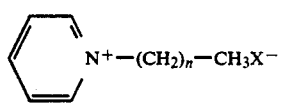

(b)

where
n is an integer of from 7 to 19,
$X^-$ is an anionic group,
said pyridinium salts having a total concentration in the range of from 0.1 to 15.0 g/l; and
said amphoteric surfactants having the formula:

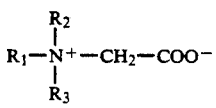

(c)

where
$R_1$ is a $C_8$ to $C_{20}$ alkyl group, and
$R_2$ and $R_3$ are $C_1$ to $C_8$ alkyl, alkenyl or alkynyl groups,
said amphoteric surfactants having a total concentration in the range of 0.1 to 15.0 g/l; and iii) at least one hemoglobin stabilizer selected from the group consisting of:
Tiron, at a concentration of 0.1 to 1000 mg/l and of the formula:

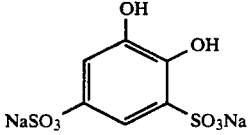

(d)

8-hydroxyquinoline, at a concentration of 0.1 to 1000 mg/l and of the formula:

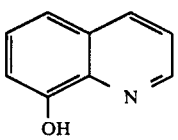

(e)

bipyridine, at a concentration of 10 to 10000 mg/l and of the formula:

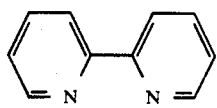 (f)

1,10-phenanthroline and its derivatives, at a concentration of 10 to 3000 mg/l and of the formula:

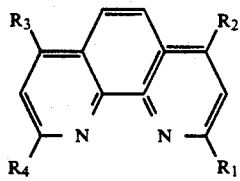 (g)

where
$R_1$ and $R_4$ are —H, —CH$_3$;
$R_2$ and $R_3$ are —H, phenyl group, —OH;
phenolic compounds, at a concentration of 0.1 to 1000 mg/l and of the formula:

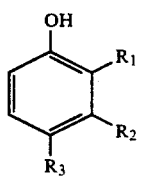 (h)

where
$R_1$ is a —H, CH$_2$OH, —CHO, —COOH or —OH,
$R_2$ is a —H, —COOH, or —OH,
$R_3$ is a —H or —COOH;
bisphenol A, at a concentration of 0.1 to 1000 mg/l and of the formula:

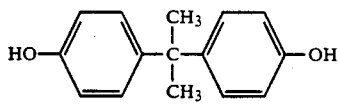 (i)

pyrazole and its derivatives, at a concentration of 0.1 to 10000 mg/l and of the formula:

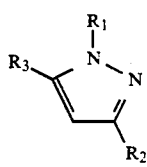 (j)

where $R_1$, $R_2$, and $R_3$ are —H or $C_1$ to $C_1$ lower alkyl groups;
a first phenyl 5-pyrazolone and its derivatives, at a concentration of 0.1 to 10000 mg/l and of the formula:

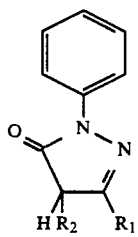 (k)

where $R_1$ and $R_2$ are —H or a $C_1$ to $C_4$ lower alkyl group;
a second phenyl 5-pyrazolone and its derivatives, at a concentration of 0.1 to 10000 mg/l and of the formula:

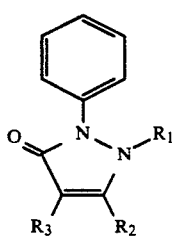 (l)

where $R_1$, $R_2$, and $R_3$ are —H or a $C_1$ to $C_4$ lower alkyl group;
phenyl 3-pyrazolone, at a concentration of 0.1 to 10000 mg/l and of the formula:

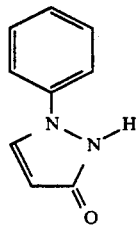 (m)

and imidazole and its derivatives, at a concentration of 1 to 20000 mg/l and of the formula:

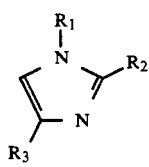 (n)

where
$R_1$ and $R_2$ are —H or a $C_1$ to $C_4$ lower alkyl group;
$R_3$ is —H or a $C_1$ to $C_4$ lower alkyl group or phenyl group.

2. The reagent according to claim 1, wherein said first surfactant has a total concentration in the range of 0.1 to 12 g/l, and said second surfactant is an amphoteric surfactant having a total concentration in the range of 0.1 to 12 g/l, and said reagent is capable of dividing leukocytes into at least two fractions.

3. The reagent according to claim 1, wherein said first surfactant has a total concentration in the range of 1 to 10 g/l, and said second surfactant is an amphoteric surfactant having a total concentration in the range of 0.1 to 10 g/l, and said reagent is capable of dividing leukocytes into three fractions.

4. The reagent according to claim 1, wherein said first surfactant has a total concentration in the range of 0.1 to 12 g/l, and said second surfactant is a pyridinium salt having a total concentration in the range of 0.3 to 10 g/l, and said reagent is capable of dividing leukocytes into at least two fractions.

5. The reagent according to claim 1, wherein said first surfactant has a total concentration in the range of 1 to 10 g/l, and said second surfactant is a pyridinium salt having a total concentration in the range of 1 to 5 g/l, and said reagent is capable of dividing leukocytes into three fractions.

6. The reagent according to claim 1, further comprising at least one additional surfactant selected from the group consisting of nonionic and cationic surfactants, said nonionic surfactant has the formula:

$$R_1-R_2-(CH_2CH_2O)_n-H \qquad (d)$$

where
$R_1$ is a $C_8$ to $C_{20}$ alkyl, alkenyl or alkynyl group,
$R_2$ is —O—,

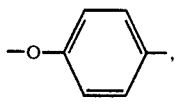

or —COO—, and
$n$ is an integer of from 10 to 50;
said nonionic surfactant having a total concentration in the range of 0.1 to 15.0 g/l, and
said cationic surfactant has the formula:

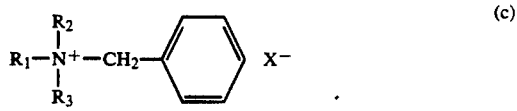

where
$R_1$ is a $C_8$ to $C_{20}$ alkyl, alkenyl or alkynyl group,
$R_2$, $R_3$ and $R_4$ is a hydrogen, $C_1$ to $C_8$ alkyl, alkenyl or alkynyl group, and
$X^-$ is an anionic group;
said cationic surfactant having a total concentration in the range of 0.1 to 15.0 g/l.

* * * * *